(12) United States Patent
Li et al.

(10) Patent No.: US 10,683,257 B2
(45) Date of Patent: *Jun. 16, 2020

(54) METHODS AND INTERMEDIATES FOR SYNTHESIZING SK1-I

(71) Applicant: Enzo Biochem, Inc., New York, NY (US)

(72) Inventors: Zaiguo Li, Little Neck, NY (US); Natarajan Raju, Germantown, MD (US); Praveen Pande, Holbrook, NY (US)

(73) Assignee: Enzo Biochem, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/410,102

(22) Filed: May 13, 2019

(65) Prior Publication Data

US 2020/0131113 A1  Apr. 30, 2020

Related U.S. Application Data

(63) Continuation of application No. 16/169,056, filed on Oct. 24, 2018, now Pat. No. 10,364,211.

(60) Provisional application No. 62/576,943, filed on Oct. 25, 2017.

(51) Int. Cl.
  *C07C 215/28* (2006.01)
  *C07C 213/08* (2006.01)
  *C07C 269/04* (2006.01)
  *C07C 269/06* (2006.01)
  *C07D 263/06* (2006.01)

(52) U.S. Cl.
  CPC .......... *C07C 215/28* (2013.01); *C07C 213/08* (2013.01); *C07C 269/04* (2013.01); *C07C 269/06* (2013.01); *C07D 263/06* (2013.01); *C07B 2200/07* (2013.01)

(58) Field of Classification Search
  None
  See application file for complete search history.

(56) References Cited

U.S. PATENT DOCUMENTS

| 8,314,151 | B2 | 11/2012 | Spiegel et al. | |
| 8,372,888 | B2 | 2/2013 | Spiegel et al. | |
| 9,388,121 | B2 | 7/2016 | Spiegel et al. | |
| 9,974,758 | B2 | 5/2018 | Spiegel et al. | |
| 10,364,211 | B1 * | 7/2019 | Li | C07C 271/16 |
| 2012/0237448 | A9 * | 9/2012 | Spiegel | C07C 217/64 424/9.2 |

OTHER PUBLICATIONS

Paugh et al., "A selective sphingosine kinase 1 inhibitor integrates multiple molecular therapeutic targets in human leukemia," *Blood*, vol. 112, pp. 1382-1391 (2008).

* cited by examiner

*Primary Examiner* — Clinton A Brooks
(74) *Attorney, Agent, or Firm* — Paul Diamond, Esq.

(57) ABSTRACT

The invention provides methods for synthesizing the compound (2R,3S,4E)-N-methyl-5-(4'-pentylphenyl)-2-aminopent-4-ene-1,3-diol, also known as SK1-I, and intermediate compounds used in its synthesis.

7 Claims, No Drawings

METHODS AND INTERMEDIATES FOR SYNTHESIZING SK1-I

CROSS-REFERENCE TO RELATED APPLICATIONS

This application is a continuation of U.S. patent application Ser. No. 16/169,056 filed Oct. 24, 2018, which claims the benefit of U.S. provisional application Ser. No. 62/576,943 filed Oct. 25, 2017 each of which is hereby incorporated by reference in its entirety.

FIELD OF THE INVENTION

The present invention relates to the field of organic synthesis of pharmaceutical compounds.

BACKGROUND OF THE INVENTION (2R,3S,4E)-N-methyl-5-(4'-pentylphenyl)-2-aminopent-4-ene-1,3-diol, also known as SK1-I and BML-258 (as HCl salt), is a pharmaceutical inhibitor of sphingosine kinase 1 initially described in Paugh et al., Blood. 2008 Aug. 15; 112(4): 1382-1391. An existing method for synthesizing SK1-I is disclosed in U.S. Pat. No. 8,314,151.

What is needed and provided by the present invention are improved methods for synthesizing SK1-I and related compounds.

SUMMARY OF THE INVENTION

One embodiment of the invention provides a method for synthesizing the compound

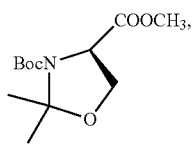

that includes the reaction steps of:
(i)

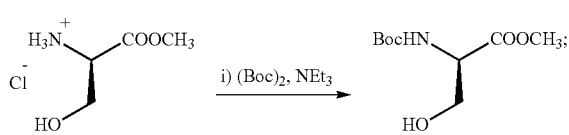

(ii)

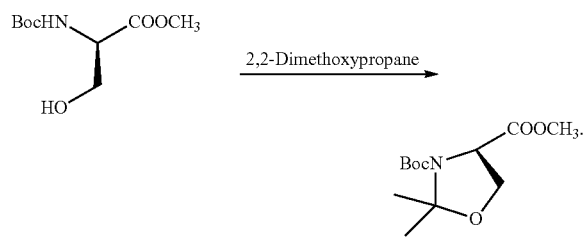

Another embodiment of the invention provides a method for synthesizing the compound

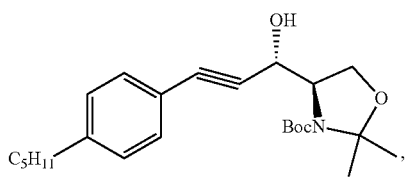

that includes the reaction step of:

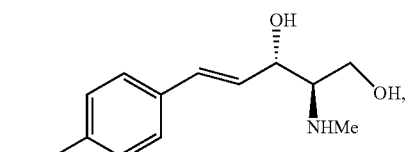

A further embodiment of the invention provides a method for synthesizing

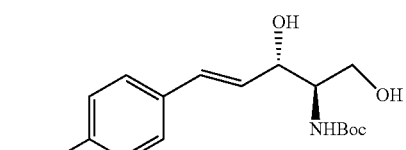

that includes the steps of:
(i) reacting

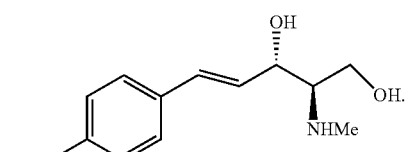

with DIBAL in the presence of Rochelle salt, thereby obtaining

[additional structure]

In one variation of this embodiment, Rochelle salt is provided in an aqueous solution that further includes sodium hydroxide.

Still further embodiments of the invention provide complete multi-step syntheses of SK1-I and salts thereof from precursor compounds.

The invention also provides corresponding embodiments in which one or more of the $C_5H_{11}$ alkyl group and the available phenyl group hydrogens are instead, independently, a linear or branched $C_{1-20}$ alkyl group or such a group having any subrange or number of carbons therein.

Additional features, advantages, and embodiments of the invention may be set forth or apparent from consideration of the following detailed description, drawings if any, and claims. Moreover, it is to be understood that both the foregoing summary of the invention and the following detailed description are exemplary and intended to provide further explanation without limiting the scope of the invention as claimed.

DETAILED DESCRIPTION OF THE INVENTION

The invention provides methods and intermediate compounds for synthesizing the compound (2R,3S,4E)-N-methyl-5-(4'-pentylphenyl)-2-aminopent-4-ene-1,3-diol, also known as SK1-I, and related compounds. The structure of SK1-I is shown below.

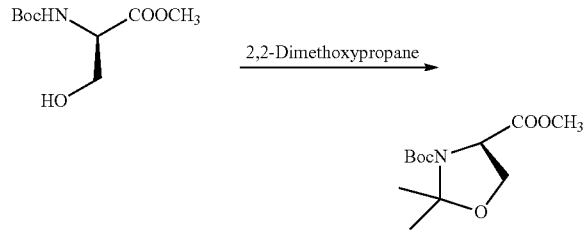

A step-wise synthesis of SK1-I according to the invention is exemplified as follows.
N-Boc-(D)-Serine Methyl Ester

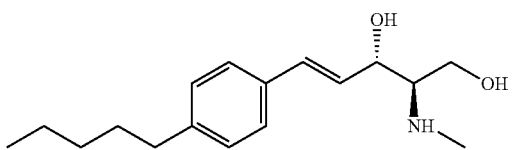 [SMILES: CCCCCc1ccc(/C=C/[C@H](O)[C@@H](CO)NC)cc1]

To an ice-cooled suspension of the (D)-Serine methyl ester hydrochloride (62.24 g, 0.4 mol) in dichloromethane (600.0 mL), triethylamine (40.4 g, 0.4 mol) was added. After the mixture was stirred for 30 min, Boc anhydride (96.0 g, 0.44 mol) in dichloromethane (100 mL) was added dropwise with vigorous stirring over 30 min. The reaction mixture was stirred for 16 hours at room temperature. Water (600 mL) was added. The organic layer was separated. The aqueous layer was extracted with 2×200 mL of dichloromethane. The combined organic layer was washed with water (2×400 mL) and dried ($Na_2SO_4$). The solution was filtered, concentrated under reduced pressure to give an oil 93.36 g (~100% yield), which was used directly in the next step without further purification.
Protection of N-Boc-(D)-Serine Methyl Ester:

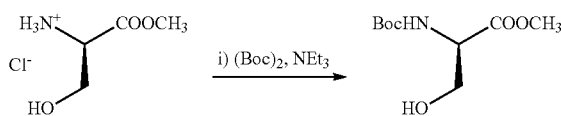 [SMILES: [Cl-] ; COC(=O)[C@H]([NH3+])CO ; COC(=O)[C@@H](CO)NC(=O)OC(C)(C)C]

Boc-Serine methyl ester from above (93.0 g, 0.42 mol) and catalyst p-toluenesulfonic acid (9.3 g) were dissolved in dichloromethane (500 mL) and 2,2-dimethoxypropane (500 mL). The mixture was stirred at room temperature for 20 hours with a drying tube. Saturated sodium bicarbonate (600.0 mL) was added. The mixture was then stirred vigorously for 30 min. The organic layer was separated, washed with bicarbonate (2×400.0 mL), water (400.0 mL), saturated NaCl (400.0 mL) and dried ($Na_2SO_4$). The solution was filtered and concentrated under vacuum to give 87.22 g oil (84% yield for two steps), which was used directly in the next step without further purification.
(R)-Garner Aldehyde:

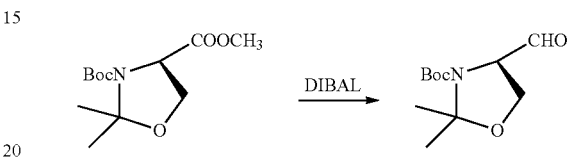

To a cooled solution of the ester (87.0 g, 0.336 mol) in anhydrous toluene (690.0 mL, −78° C., acetone/dry ice bath), DIBAL in toluene (1.49 M in toluene, 392 mL, 585.0 mmol) was added dropwise under argon in such a way that the internal temperature did not rise above −70° C. After the addition, the reaction mixture was stirred for an additional 4 hours at −78° C. Methanol (128 mL) was added to the mixture to quench the reaction. The mixture was poured slowly into an aqueous solution of Rochelle salt (potassium sodium tartrate tetrahydrate; 1.2 M, 660 g/1949 mL water) with vigorous stirring. The mixture was stirred at room temperature until clear separation into two layers. The aqueous layer was extracted with diethyl ether (2×300.0 mL). The combined organic layer was washed with water (2×800 mL) and brine (800 mL), then dried with anhydrous $Na_2SO_4$. The solvent was evaporated under vacuum to give aldehyde as a pale yellow oil (68.59 g, 89%), which was used without further purification.
Addition of 4-Pentylphenyl Acetylene to the Above Aldehyde:

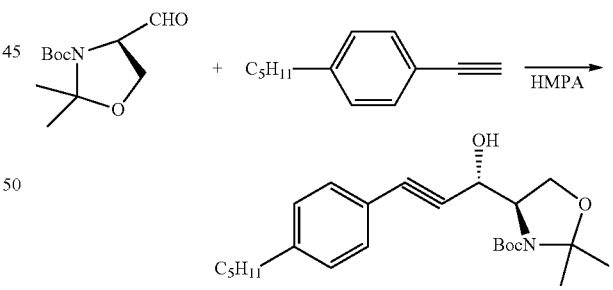

To a cooled (−20° C.) solution of 4-n-pentylphenylacetylene (51.68 g, 300 mmol) in dry THF (400 mL), n-BuLi solution (2.5 M in hexane, 120 mL, 300 mmol) was added dropwise under argon. After 2 hours, the mixture was cooled to −78° C., followed by the addition of HMPA (hexmethylphosphoramide, 64.5 g, 360 mmol). After the mixture was stirred at −78° C. for an additional 30 mins, methyl (R)-(+)-3-(t-butoxycarbonyl)-2,2-dimethyl-4-oxazolidinecarboxaldehyde (58.0 g, 248.3 mmol) in anhydrous THF (tetrahydrofuran; 100 mL) was added dropwise (maintaining the temperature below −60° C.). The mixture was stirred for an additional 5 hours at −78° C., then quenched by saturated ammonium chloride solution (1000 mL). The aqueous layer was extracted with ethyl ether (3×400 mL). The combined organic layer was washed with 0.5 N HCl (2×400 mL) and brine (400 mL), then dried with anhydrous sodium sulfate. The solvent was removed under vacuum to give a yellow oil (104.04 g, ~100% yield), which was used without further purification.

Deprotection of the Above Oxazolidine:

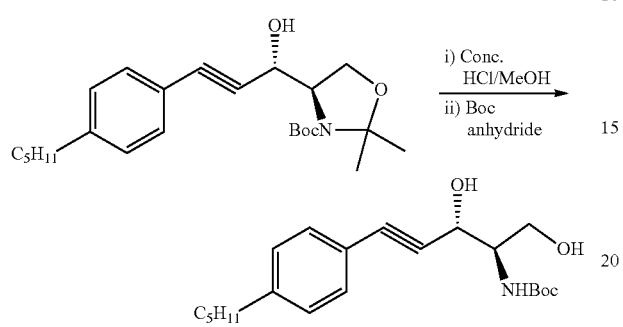

To an ice cooled solution of Boc-oxazolidine (103.0 g, 257.0 mmol) in methanol (1000 mL), was added conc. HCl (43.5 mL, pre-cooled to 0° C.). The mixture was stirred at room temperature overnight and then extracted with hexane (3×400 mL). The pH of the methanol solution was adjusted with solid sodium bicarbonate to 8.0. Boc anhydride (53.94 g, 245.92 mmol) was added and the mixture was stirred at room temperature for 1-4 hours until the disappearance of formed intermediate free amine. The solvent was removed under vacuum. The residue was redissolved in water (300 mL) and diethyl ether (300 mL). The ethyl ether layer was dried with anhydrous sodium sulfate and then evaporated to give a brown oil (87.54 g, 94%), which was used without further purification.

Reduction of the Above Alcohol:

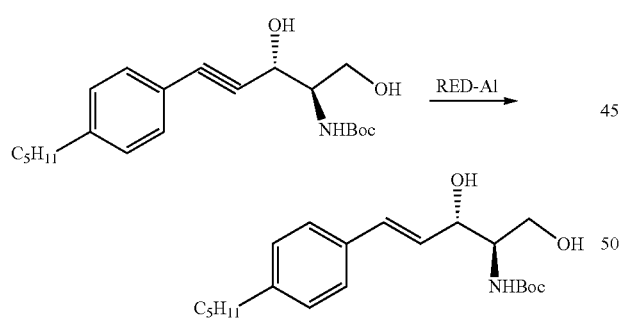

To an ice-cooled solution of the above acetylene (87.0 g, 241.0 mmol) in THF (800 mL), Red-Al (Sodium bis(2-methoxyethoxy)aluminum dihydride; 60% w/w in toluene, 392 mL; 1.205 mol) was added dropwise over 1 hour under argon with stirring. The solution was then stirred at room temperature for 36 hours. The reaction mixture was cooled in an ice bath and then poured carefully into a pre-cooled solution of Rochelle salt in water (700 g in 2200 mL of water). The mixture was vigorously stirred until two layers were visible and well separated. The aqueous layer was extracted with 2×600 mL of toluene. The combined toluene layer was washed with water (2×800 mL) and saturated sodium chloride (800 mL) and dried (Na$_2$SO$_4$). The solvent was removed under vacuum to give a yellowish semi solid, which was recrystallized with hexane (200 mL) to give a white solid 43.3 g (purity: >98%; yield: 49%)

Deprotection to SK1-I (BML-258):

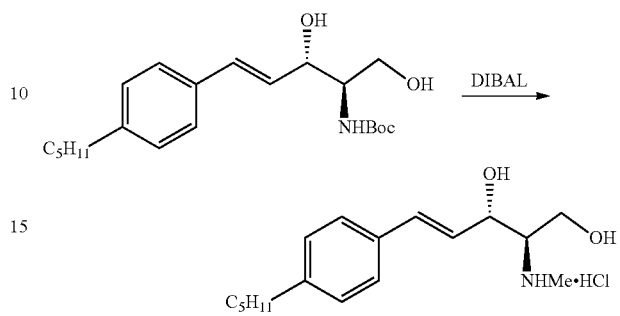

To a solution of Boc protected amine (15 g, 41.3 mmol) in anhydrous THF (300 mL), DIBAL (25% w/w in toluene, 1.49 M, 278 mL, 413 mmol) was added at room temperature under argon. The mixture was refluxed until the starting material disappeared. The mixture was cooled to room temperature and poured into Rochelle salt (340 g/1000 mL water) containing sodium hydroxide (50 g, ~5%). The mixture was stirred vigorously for 1 hour. The aqueous layer was extracted with ethyl acetate (2×500 mL). The combined organic layer was washed with water (1000 mL) and brine (1000 mL) and dried with anhydrous sodium sulfate. The solvent was removed under vacuum to afford yellowish oil, which turned into a pale solid after storing at −20° C. overnight. To a cold solution (ice bath) of this solid in ethyl ether (400 mL), was added 1M HCl in ethyl ether (50 mL). The white precipitate was collected by filtration and washed with ethyl ether (2×50 mL), and then dried under vacuum to give product as a white solid (8.11 g, 63% yield).

Advantageous improvements obtained in this synthesis of SK1-I include the following. First, introducing HMPA in the coupling of Garner aldehyde with acetylene improves the ratio of the desired erythro isomer (versus undesired threo-isomer) to ~20:1 (from ~8:1 without HMPA), thus eliminating the prior necessity of column purification to remove undesired isomer (threo-). Second, introducing Rochelle salt during the work up at the DIBAL reduction of Boc to a methyl group (last step) increased the yield of the pure product. And third, through a few modifications in different steps, the prior necessity for flash column purification was eliminated.

It should be understood that the synthesis described herein may be readily adapted for any derivative in which the C$_5$H$_{11}$ group is replaced by a different alkyl group. For example, the invention provides corresponding embodiments in which the C$_5$H$_{11}$ alkyl group is instead a linear or branched C$_{1-20}$ alkyl group or such a group having any subrange or number of carbons therein. The invention also provides corresponding embodiments in which one or more of the C$_5$H$_{11}$ alkyl group and the available hydrogen positions of the phenyl ring (together corresponding to positions R$_1$ through R$_5$ in the final compound generic formula printed below) independently have, instead of said group or hydrogen respectively, a linear or branched C$_{1-20}$ alkyl group or such a group having any subrange or number of carbons therein.

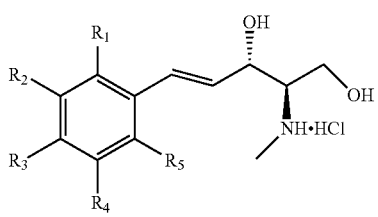

It should also be understood that in this disclosure and the appended claims where sequential reaction steps are graphically depicted that the output of a reaction step is the input of the next step. It should also be understood that wherever initial reactants are shown, such reactants may be provided in a providing step.

Any and all publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s). Moreover, features described in connection with one embodiment of the invention may be used in conjunction with other embodiments, even if not explicitly exemplified in combination within.

What is claimed is:

1. A method for synthesizing the compound

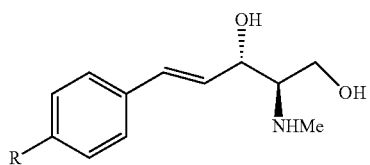

in which R is an alkyl group, comprising the reaction steps of:

(i)

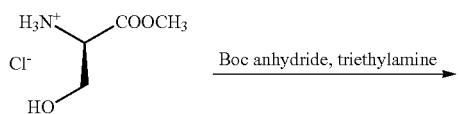

(ii)

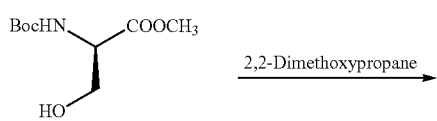

(iii)

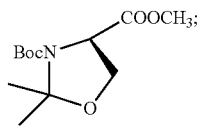

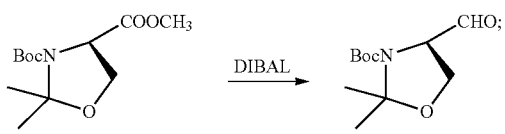

(iv)

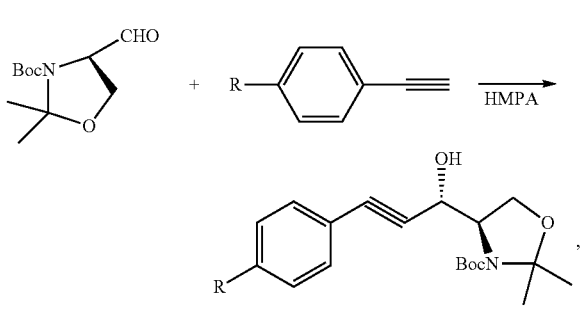

wherein R is a $C_{1-20}$ alkyl group;

(v)

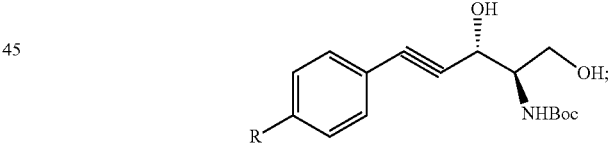

(vi)

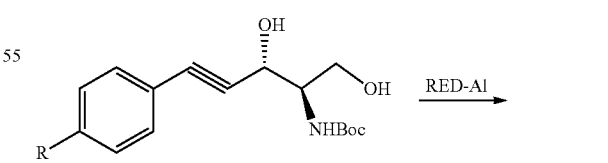

and (vii) reacting

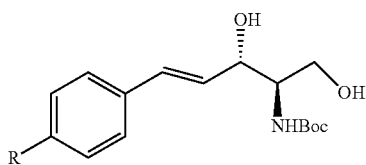

with DIBAL in the presence of Rochelle salt, thereby obtaining

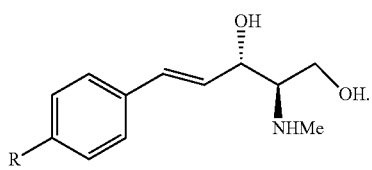

2. The method of claim 1, wherein R is a linear alkyl group.

3. The method of claim 1, wherein R is a branched alkyl group.

4. The method of claim 1, wherein step (vii) comprises the substeps of:
   (a) adding

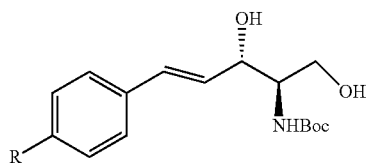

to DIBAL to form a reaction mixture, and
   (b) adding the reaction mixture to a solution comprising Rochelle salt.

5. The method of claim 4, wherein R is a linear alkyl group.

6. The method of claim 5, wherein R is a $C_5H_{11}$ group.

7. The method of claim 4, wherein R is a branched alkyl group.

\* \* \* \* \*